(12) United States Patent
Comstock et al.

(10) Patent No.: US 10,646,257 B2
(45) Date of Patent: May 12, 2020

(54) ABRADING IMPLEMENT

(71) Applicants: Scott Comstock, La Canada, CA (US); Kurt Comstock, Sylmar, CA (US)

(72) Inventors: Scott Comstock, La Canada, CA (US); Kurt Comstock, Sylmar, CA (US)

( * ) Notice: Subject to any disclaimer, the term of this patent is extended or adjusted under 35 U.S.C. 154(b) by 0 days.

(21) Appl. No.: 14/687,376

(22) Filed: Apr. 15, 2015

(65) Prior Publication Data

US 2015/0297261 A1 Oct. 22, 2015

Related U.S. Application Data

(60) Provisional application No. 61/980,799, filed on Apr. 17, 2014.

(51) Int. Cl.
*A61B 17/54* (2006.01)
*A61B 17/32* (2006.01)
*A61B 17/00* (2006.01)

(52) U.S. Cl.
CPC ...... *A61B 17/54* (2013.01); *A61B 2017/0046* (2013.01); *A61B 2017/320004* (2013.01); *A61B 2017/320008* (2013.01)

(58) Field of Classification Search
CPC . Y10S 451/912; Y10S 451/903; B24D 15/04; B24D 15/023; B24D 15/02; B24D 18/0009; B24D 18/0081; B24D 3/007; B23D 71/00; B23D 67/12; A61B 2017/320008; A61B 2017/320004; A61B 2017/0046; A61B 17/54; A61B 2017/00774; A61B 2017/00761; A47J 43/25; A45D 29/17; A45D 29/14; A45D 29/12; A45D 29/11; A45D 29/05; A45D 29/04; A45D 29/00; A45D 2200/1054; A45D 2029/045
USPC ......... 451/523; 132/76.5, 76.4, 75, 75.6, 73; 606/131; D28/56–57, 59
See application file for complete search history.

(56) References Cited

U.S. PATENT DOCUMENTS

| | | | | |
|---|---|---|---|---|
| 1,416,619 A | * | 5/1922 | Davis | A45D 29/11 132/76.5 |
| 1,643,164 A | * | 9/1927 | MacDougall | A45D 29/11 132/74.5 |
| 1,679,603 A | * | 8/1928 | Clemenger | A45D 29/11 132/75 |
| 1,955,848 A | * | 4/1934 | Dunn | B24D 15/088 76/81.8 |
| 2,036,107 A | * | 3/1936 | Thomas | B24D 15/023 451/503 |
| 2,225,567 A | * | 12/1940 | Neuschaefer | A45D 29/04 132/76.4 |
| 2,527,089 A | * | 10/1950 | Adams | B24D 15/023 451/515 |
| 2,802,317 A | * | 8/1957 | Stuck | B24D 15/02 451/554 |

(Continued)

*Primary Examiner* — Yogesh P Patel
*Assistant Examiner* — Jennifer F Gill
(74) *Attorney, Agent, or Firm* — James A. Italia; Italia IP (57) ABSTRACT

An abrading implement for abrading surfaces comprises a multi-part, hollow holder and a flexible abrasive stratum secured within the holder. The abrasive stratum is flexible or deformable, and protrudes from the holder. A form internal to the abrading implement bears against the abrasive stratum to cause the abrasive stratum to protrude from the holder. The abrasive stratum may be perforated and coated with an abrasive such as silicon carbide.

9 Claims, 5 Drawing Sheets

(56) References Cited

U.S. PATENT DOCUMENTS

| | | | | |
|---|---|---|---|---|
| 3,681,806 A * | 8/1972 | Han | ............ | A47K 5/03 |
| | | | | 15/105 |
| 3,706,316 A * | 12/1972 | Konagai | ............ | A45D 29/11 |
| | | | | 132/76.4 |
| 3,769,760 A * | 11/1973 | Kritske | ............ | B24D 15/02 |
| | | | | 451/540 |
| 4,377,057 A * | 3/1983 | Pincha | ............ | B24D 15/023 |
| | | | | 451/491 |
| 5,730,645 A * | 3/1998 | Park | ............ | B24B 31/14 |
| | | | | 451/32 |
| 2007/0225732 A1* | 9/2007 | Cho | ............ | A61B 17/54 |
| | | | | 606/131 |
| 2008/0091216 A1* | 4/2008 | Grace | ............ | A61B 17/54 |
| | | | | 606/131 |
| 2011/0015463 A1* | 1/2011 | Legendre | ............ | A45D 40/00 |
| | | | | 600/9 |
| 2013/0269205 A1* | 10/2013 | Hada | ............ | A45D 20/10 |
| | | | | 34/283 |
| 2013/0345721 A1* | 12/2013 | Menke | ............ | A61B 17/54 |
| | | | | 606/131 |
| 2015/0122282 A1* | 5/2015 | Hada | ............ | A45D 20/10 |
| | | | | 132/200 |
| 2018/0235661 A1* | 8/2018 | Palushaj | ............ | A45D 29/00 |

* cited by examiner

ABRADING IMPLEMENT

CROSS REFERENCE TO RELATED APPLICATION

The present application claims priority benefit of the U.S. Provisional Application Ser. No. 61/980,799, filed on Apr. 17, 2014. The subject matter of the aforementioned application is incorporated herein by reference for all purposes to the extent that such subject matter is not inconsistent herewith or limiting hereof.

FIELD OF THE DISCLOSURE

The present disclosure relates to hand held abrading implements.

BACKGROUND

Many people suffer from dry skin, particularly on the hands and the feet. Such a condition is often more pronounced in dry climates with low humidity levels. In extreme instances, a person's skin, and particularly the heels, can even become cracked while producing numerous additional layers of hardened skin.

There are numerous health and beauty products available that aid in removing or exfoliating dead skin from areas of the body. For example, pumice stones and other abrasive devices are available to exfoliate, smooth and eliminate dry or dead skin. Such devices sand the area to be exfoliated in a back and forth or circular motion to remove the dry or dead skin cells. However, such products may not exfoliate a substantial quantity of dry or dead skin while simultaneously sanding the area. When such devices are used, the exfoliated skin cells may accumulate between the area and the abrasive surface, which greatly reduces the friction between the two surfaces. The exfoliated waste may also become trapped in pits within the cracks of the skin as well as minute openings and crevices within the exfoliating device itself. Such conditions result in a degradation in the exfoliating device's effectiveness.

SUMMARY

The disclosed concepts provide an abrading implement which addresses the above stated shortcomings of many conventional abrading tools. The abrading implement comprises an abrading element which protrudes from a hand gripped holder. A space is left on the non-working side of the abrading element for receiving abraded skin residue, thereby overcoming clogging of the abrading element. The abrading implement has features for clearing skin residue therefrom.

It is an object to provide improved elements and arrangements thereof by abrading implement for the purposes described which is inexpensive, dependable, and fully effective in accomplishing its intended purposes.

These and other objects will become readily apparent upon further review of the following specification and drawings.

BRIEF DESCRIPTION OF THE DRAWINGS

Various objects, features, and attendant advantages of the disclosed concepts will become more fully appreciated as the same becomes better understood when considered in conjunction with the accompanying drawings, in which like reference characters designate the same or similar parts throughout the several views, and wherein.

DETAILED DESCRIPTION

Referring to FIGS. 1-6, according to at least one aspect of the disclosure, there is shown a an abrading implement 100 for abrading a surface (not shown). Abrading implement 100 comprises a holder 102 comprising a frame 104 having a central opening 106. A wall 108 bounds central opening 106. Frame 104 has a first end 110, and an opposed second end 112. Holder 102 includes a cap 114 covering central opening 106 at the opposed second end 112 of frame 104. Abrading implement 100 comprises an abrasive stratum 116 to be held by holder 102. Abrasive stratum 116 occupies central opening 106 and protrudes from first end 110 of frame 104 he open center of cap 114 extends to abrasive stratum 116.

Unless otherwise indicated, the terms "first", "second", etc., are used herein merely as labels, and are not intended to impose ordinal, positional, or hierarchical requirements on the times to which these terms refer. Moreover, reference to, e.g., a "second" item does not either require or preclude the existence of, e.g., a "first" or lower-numbered item, and/or, e.g., a "third" or higher-numbered item.

Figure 1:
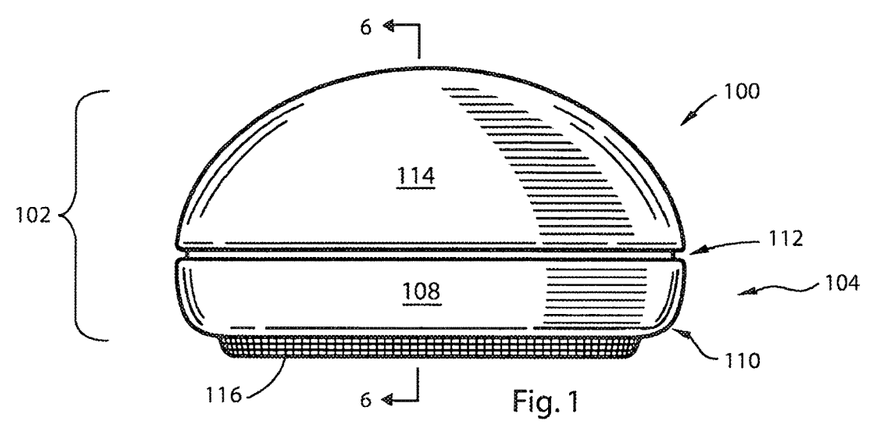
FIG. 1 is a side view of an abrading implement, according to at least one aspect of the disclosure.
Figure 2:
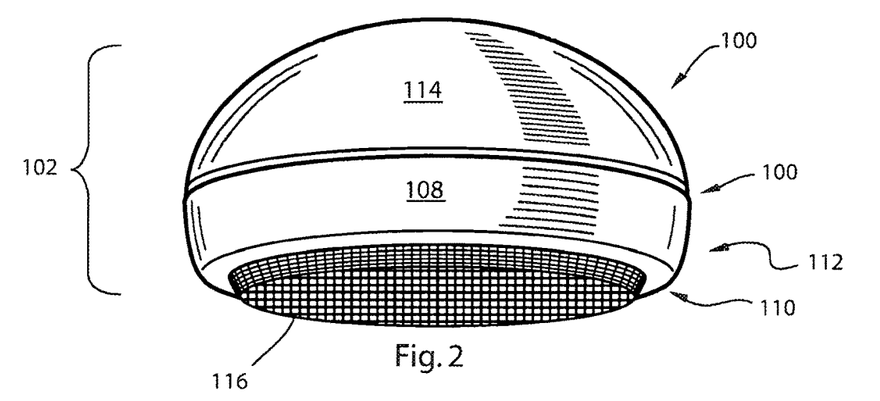
FIG. 2 is a bottom perspective view of the abrading implement of FIG. 1, according to at least one aspect of the disclosure.
Figure 3:
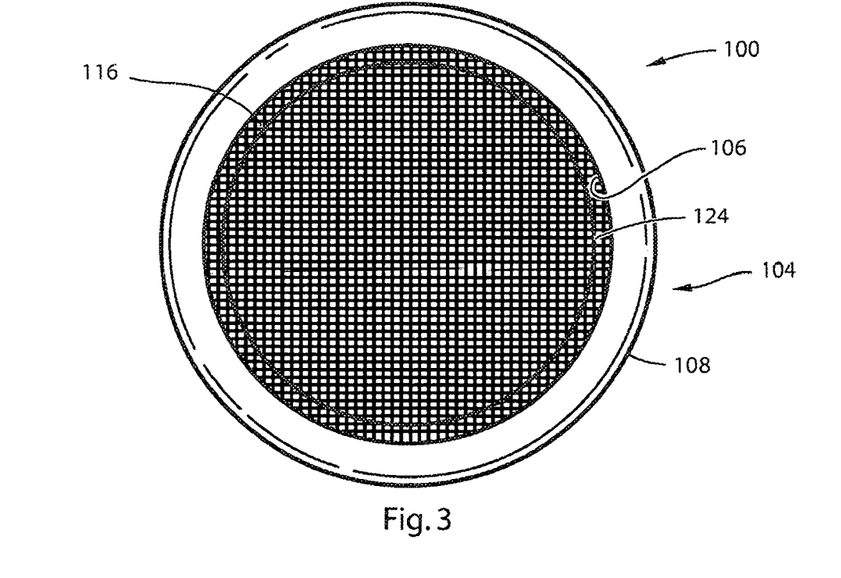
FIG. 3 is a bottom plan view of the abrading implement of FIG. 1, according to at least one further aspect of the disclosure.

Abrasive stratum 116 is somewhat flexible, being able to conform to curvature and contours of the human hand and foot, for example, while still generally holding the configuration depicted in FIG. 1. Abrasive stratum 116 may have a blunt border 124 of soft material (FIG. 2). Blunt border 124 protects users of abrading implement 100 from potentially sharp edges of abrasive stratum 116. Blunt border 124 may cover at least a portion or all of the circumference of abrasive stratum 116. Blunt border 124 may be formed from a synthetic foam, a flexible natural or synthetic plastics and rubbers, a bead of silicone, or other suitable material.

Blunt border 124 may be secured to abrasive stratum 116 by an adhesive such as cyanoacrylate adhesive (i.e., so-called "super glue"), hot glue or any other adhesive adapted to bond blunt border 124 to abrasive stratum 116.

Holder 102 includes a first connector and a second connector enabling cap 114 to be removably coupled to frame 104. The first connector and the second connector may comprise screw threads 120, 122. Alternatively, the first and second connectors may comprise a bayonet connection, friction fit, friction pins, and other known mechanical couplings (none shown).

Abrasive stratum 116 is deformable. Holder 102 includes a form 118 configured to shape abrasive stratum 116 to protrude from first end 110 of frame 104. Ridge 128 engages abrasive stratum 116 about opening 106 near wall 108, causing abrasive stratum 116 to bulge downwardly (as seen in FIG. 1) when abrading implement 100 is assembled. This bulging causes abrasive stratum 116 to protrude from wall 108 sufficiently such that abrasive stratum 116 contacts a surface being abraded and wall 108 does not contact that surface under mild manual forces ordinarily encountered when abrading dry skin. Ordinarily encountered forces are for example within a range of one to three pounds of force.

Frame 104, cap 114, and form 118 may be fabricated from a suitable plastic such as nylon, acrylonitrile butadiene styrene, and others, or from any synthetic resin, metal, wood, ceramic material, still other materials, and combinations of these.

At least one of cap 114 and form 118 includes a plurality of nubs 126 configured to engage abrasive stratum 116 and to compress abrasive stratum 116 against second end 112 of frame 104 when holder 102 is assembled.

Figure 4:
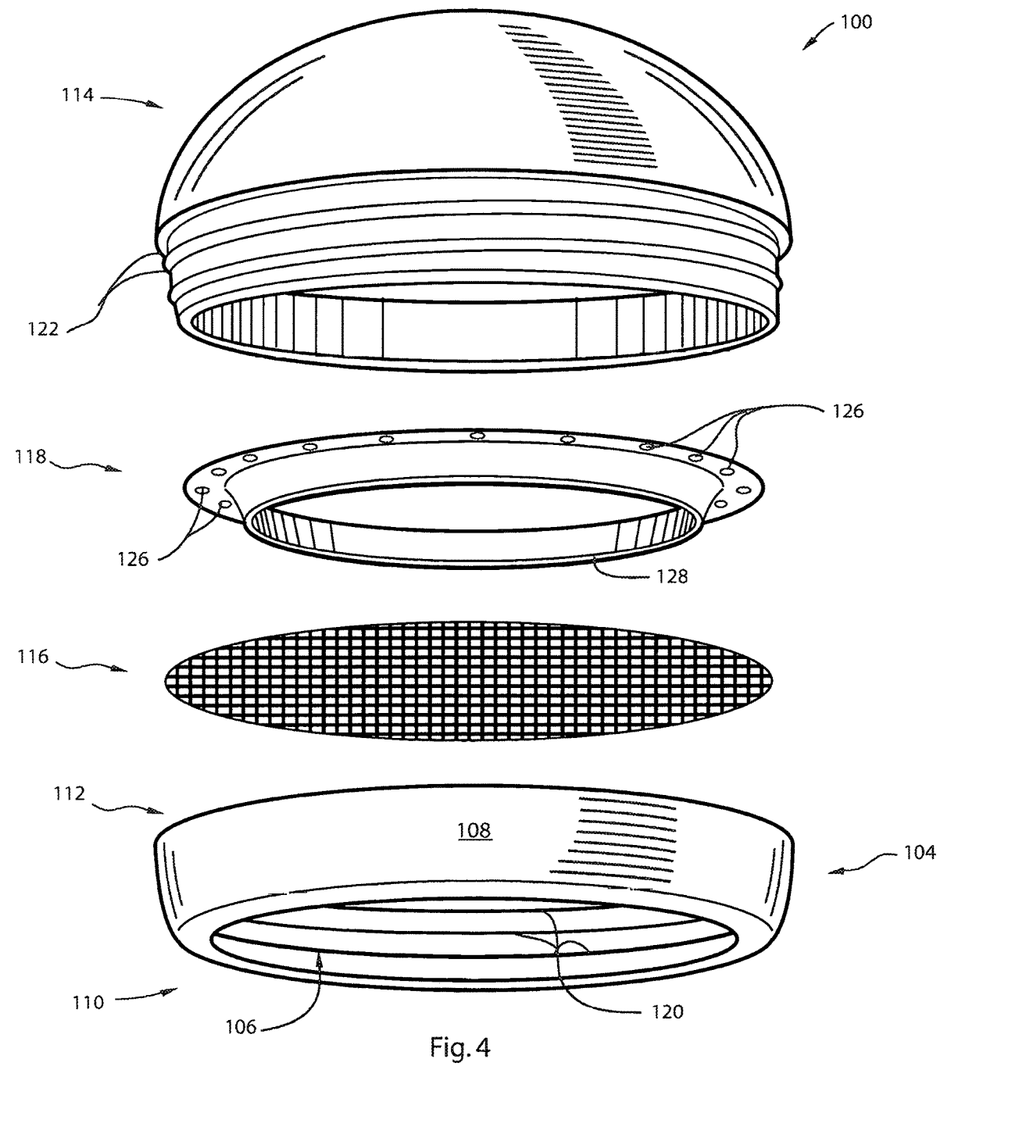
FIG. 4 is an exploded perspective view of the abrading implement of FIG. 1.
Figure 6:
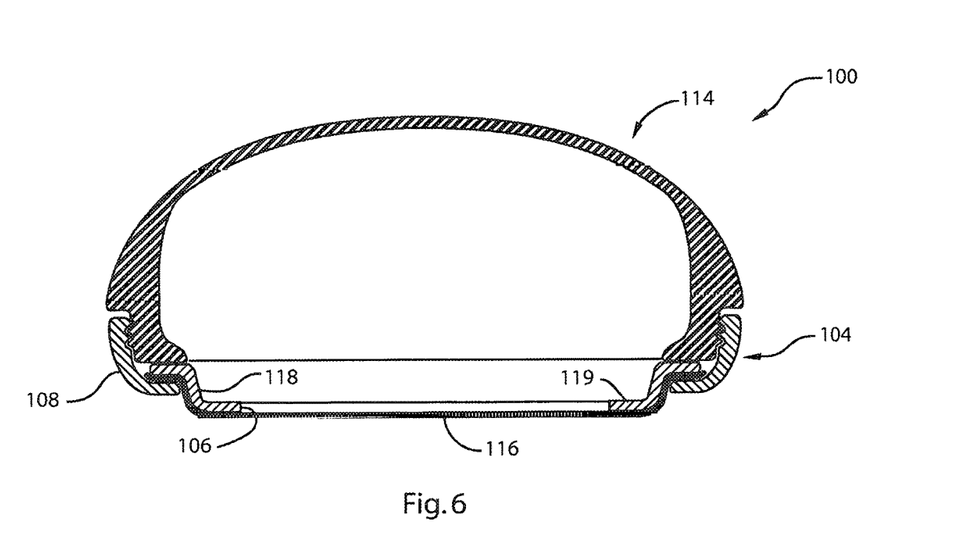
FIG. 6 is a side cross sectional view of the abrading implement shown along the line 6-6 in FIG. 1.

As depicted in FIG. 4 and FIG. 6, form 118 is separate from cap 114 and frame 104, and is held in place by entrapment between frame 104 and cap 104. Cap 114 and wall 108 of frame 104 are configured to surround and entrap form 118 by interference fit between cap 114 and wall 108 of frame 104. An advantage of this arrangement is that form 118 is replaceable, and can be renewed if broken or defective, cleaned, or replaced with a form 118 of different dimensions and/or configuration.

Figure 5:
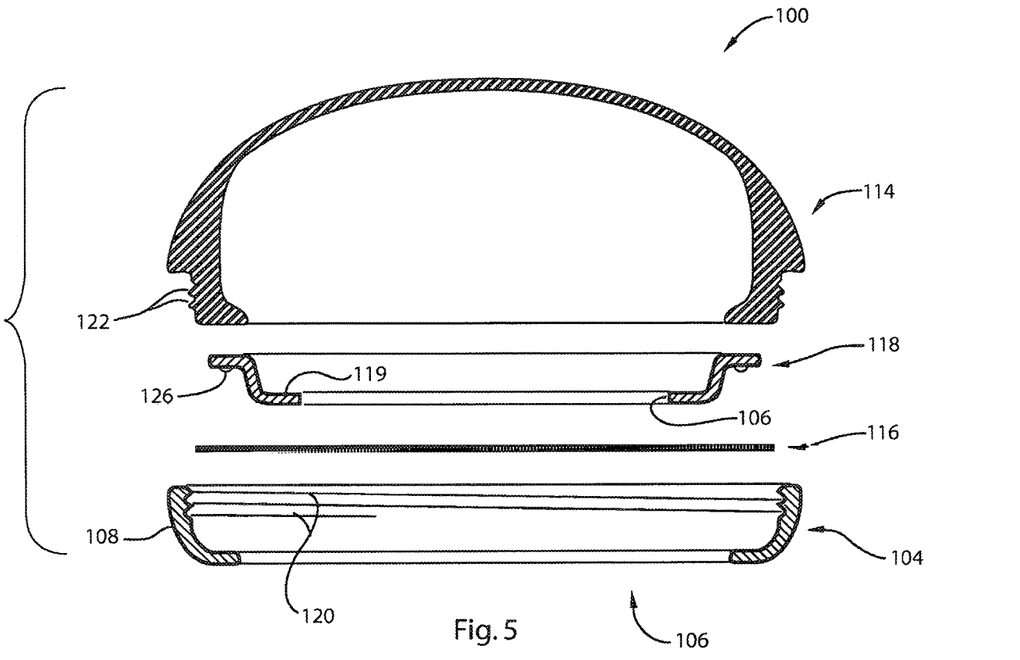
FIG. 5 is an exploded side cross sectional view of the abrading implement shown in FIG. 6, according to at least a further aspect of the disclosure.

An abrading implement 100 shown in FIGS. 5 and 6 is generally similar to that of FIGS. 1-4, except that form 118 includes an inwardly directed flange 119. Flange 119 reduces unit loads imposed against abrasive substrate 116, and narrows central opening 106.

Figure 7:
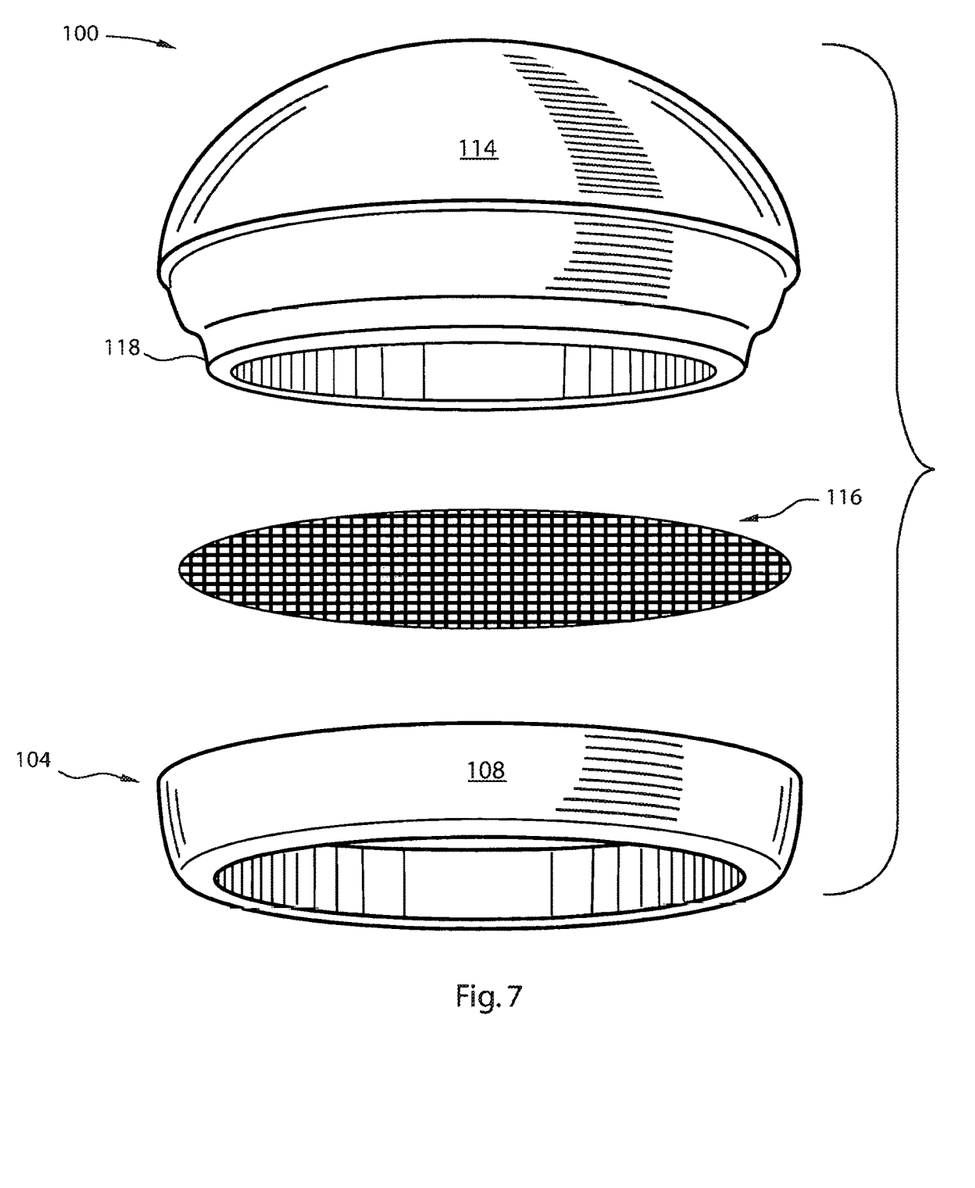
FIG. 7 is an exploded perspective view of an abrading implement, according to at least yet another aspect of the disclosure.

As an alternative, and referring momentarily to FIG. 7, form 118 is integral with cap 114. This may be accomplished for example by molding form 118 and cap 114 integrally, or by bonding form 118 to cap 114, such as by adhesive, fusing form 118 to cap 114 using a solvent, by sonic welding, or in any other suitable way.

Figure 8:
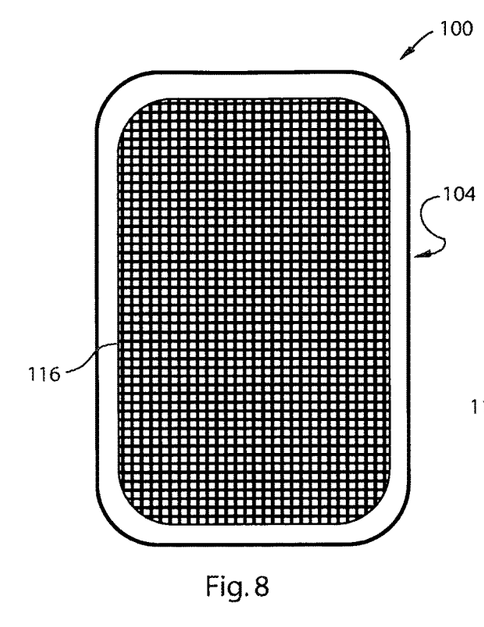
FIG. 8 is a bottom plan view of an abrading implement, according to at least a further aspect of the disclosure.
Figure 9:
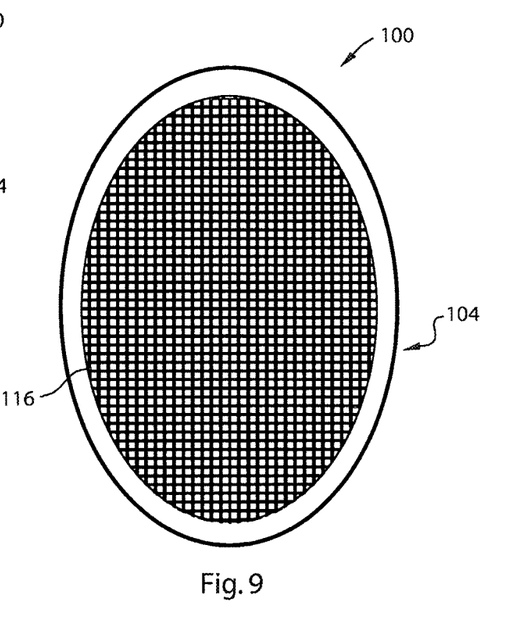
FIG. 9 is a bottom plan view of an abrading implement, according to at least a further aspect of the disclosure.

As seen in FIG. 2, frame 104 is circular when viewed from first end 110. Of course, other configurations, such as rectangular (e.g., FIG. 8), triangular, hexagonal, oval (FIG. 9), elliptical, and irregular (some of these options are not shown) are possible.

Cap 114 may be domed. If domed, cap 114 is comfortably grasped in the palm of a person using abrading implement 100.

To this end, cap 114 may have a diameter (if circular, as shown in FIG. 2) or maximum transverse dimension (if not circular) in the range of two to five inches. In an exemplary implementation of abrading implement 100, area of abrasive stratum may be sixteen square inches, or approximately four-by-four inches in size. A four-by-four device allows the screen to be small enough to fit in the palm of a person's hand, yet large enough to cover a substantial part of the surface area of the location of the body to be exfoliated. Where the above dimensions are used in an abrading implement 100, blunt border 124 may be approximately three thirty-seconds of an inch thick, one inch wide and may extend the length of each side of abrasive substrate 116. The width of blunt border 124 is adapted to accommodate folding over an associated edge of the abrasive substrate 116 so that both the top surface and bottom surface of the latter are covered and thereby protected. If the total thickness of blunt border 124 is, for example, one inch thick prior to folding over an edge of abrasive substrate 116, then blunt border 124 extends approximately one half inch inwardly from the edge of abrasive substrate 116 on both the top surface and bottom surface.

Although abrasive stratum 116 may be imperforate, such as if provided as a product such as sandpaper, abrasive stratum 116 may be perforated. For example, abrasive stratum 116 may comprise a porous mesh, for example of the type used to abrade gypsum based drywall. Pore size is sufficient to efficiently pass removed skin residue through abrasive stratum 116, so that abrasive stratum 116 will not become clogged or fouled by skin residue. Where cap 114 is removable from frame 104, captured skin residue is readily removed. As an alternative to disassembly of abrading implement 100, cap 114 may be provided with openings so that skin residue may be removed by flushing with water, removal by vacuum, by air blasting, by gravity, using vibration, such as by manually tapping on abrading implement 100, or in any other suitable way.

Figure 10:
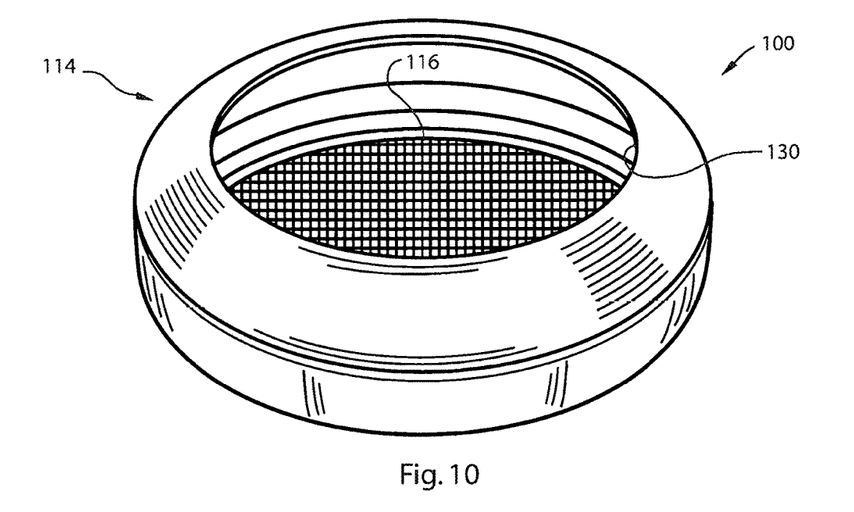
FIG. 10 is a perspective view of an abrading implement, according to still a further aspect of the disclosure.

Turning to FIG. 10, cap 114 may have a central opening 130. This enables skin residue to be removed by inverting abrading implement 100 and tapping, shaking, air blasting, flushing, etc. Central opening 130 may alternatively comprise a plurality of openings smaller than that shown in FIG. 10.

Whether perforate or imperforate, abrasive stratum 116 may comprise a coating of silicon carbide to provide abrasive qualities.

Frame 104, cap 114, or both may include external nubs (not shown) to improve manual grasp and oppose slippage when abrading implement 100 is being used.

In use, abrasive stratum 116 is placed over an area of the body from which skin is to be exfoliated. Under normal conditions, a person's skin comprises a statum corneum, or outermost skin layer, that has approximately fifteen to twenty layers of dead skin cells. Typically, this equates to a thickness of ten to twenty microns. A person with dry and callused feet, for example, can have a statum corneum with a thickness of one hundred to one hundred fifty microns. Typically, for a pedicure, the pedicurist uses a razor to remove the additional layers of skin. Such an operation, however, is uncomfortable and sometimes painful for the person receiving the skin treatment. In some cases, the razor device can cut too deeply causing injury or bleeding, but most often leaves the feet feeling raw and tender. Abrading implement 100 exfoliates the additional seventy to one hundred thirty microns of dead skin cells by successively removing each layer, but without the pain associated with use of a razor or similar type product.

During an exfoliating operation, continuous contact is maintained between the skin and abrasive substrate 116. This allows abrading implement 100 to exfoliate multiple layers of dry or dead skin cells as each successive layer of skin is removed and passes through the screen member device.

Abrading implement 100 is placed in the palm of a person's hand. The user then presses abrading implement 100 against the area of the body to be exfoliated. A back-and-forth or circular motion applied to abrading implement 100 removes the dead skin. The amount of pressure may vary depending on how much skin is to be removed. The greater the pressure increases the amount of skin removed. The exfoliated skin passes through abrasive substrate 116 and is trapped within abrading implement 100, away from the surface of abrasive substrate 116 that contacts the area to be exfoliated. In an alternative operation, abrading implement 100 comprises a two-sided abrasive substrate 116 wherein both sides have an abrasive material disposed thereon. Either side may be pressed against the area to be exfoliated.

A user may also utilize a lower grit number (or high coarseness) to remove large amounts of skin, yet leaving a coarse finish. A user may then follow up with a higher grit number (less coarseness) to remove less skin but, leave a smoother finish on the exfoliated area, such as the heel. A user may then apply moisturizer after exfoliating to further soften the skin.

Typically, for the most effective use of abrading implement 100, the area to be exfoliated should be dry when removing dead or dry skin from the area. Accordingly, it is recommended a period of time pass after the area has been washed or moisturized before using abrading implement 100. A wet or moist area may result in the exfoliated skin cells clogging the holes in abrasive substrate 116. A abrading implement 100 may be used once and then discarded, as continued use of abrading implement 100 may reduce its effectiveness for exfoliating dead or dry skin cells. Alternatively, abrasive substrate 116 may be replaced, so that abrading implement 100 may be used more than once.

Abrading implement 100 has been described in terms of exfoliation of human skin. However, abrading implement 100 may find other uses, such as in wood finishing, automotive body repairs, and any endeavor wherein surfaces, particularly curved surfaces, are to be abraded.

While the disclosed concepts have been described in connection with what is considered the most practical and preferred implementation, it is to be understood that the disclosed concepts are not to be limited to the disclosed arrangements, but are intended to cover various arrangements which are included within the spirit and scope of the broadest possible interpretation of the appended claims so as to encompass all modifications and equivalent arrangements which are possible.

It should be understood that the various examples of abrading implement 100 disclosed herein may include any of the components, features, and functionalities of any of the other examples of abrading implement 100 disclosed herein in any feasible combination. All of such possibilities are intended to be within the spirit and scope of the present disclosure. Many modifications of examples set forth herein will come to mind to one skilled in the art to which the present disclosure pertains having the benefit of the teachings presented in the foregoing descriptions and the associated drawings.

Therefore, it is to be understood that the present disclosure is not to be limited to the specific examples presented and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims.

We claim:

1. An non-motorized abrading implement for abrading a surface, comprising:
a holder comprising a dome-shaped cap, wherein the cap includes an integral form such that the cap and the form are unified as one part, and a frame having a central opening, a first end, and an opposed second end; and
an abrasive stratum configured for removing material from the surface, such that an amount of material that is removed from the surface increases in response to increased pressure applied to the abrasive stratum upon the surface, the abrasive stratum to be held by the holder between said integral form of said cap and the frame when the holder is assembled, the abrasive stratum including a center portion and a periphery, wherein the integral form of said cap and the frame engage and contact the abrasive stratum only at the periphery of the abrasive stratum, wherein the form includes a portion that portrudes out and away from the frame and away from the cap through the central opening of the frame such that it is configured to abut only the periphery of the abrasive stratum and to shape the center portion of the abrasive stratum to protrude out and away from the frame and away from the cap,
wherein said center portion of said abrasive stratum is unsupported by any underlying structure and deformable relative to said periphery of the abrasive stratum, which is supported by said form.

2. The abrading implement of claim 1, wherein:
the cap is removably coupled to the frame via a first and second connectors.

3. The abrading implement of claim 2, wherein the first and second connectors are screw threads.

4. The abrading implement of claim 1, wherein the frame is circular when viewed from the first end.

5. The abrading implement of claim 1, wherein the abrasive stratum is perforated.

6. The abrading implement of claim 1, wherein the abrasive stratum is disk shaped.

7. A non-motorized abrading implement for abrading a surface, comprising:
a holder comprising a dome-shaped cap, a frame, and a form positioned between the cap and frame when the holder is assembled; and
an abrasive stratum configured for removing material from the surface, such that an amount of material that is removed from the surface increases in response to increased pressure applied to the abrasive stratum upon the surface, the abrasive stratum to be held by the holder between the form and the frame when the holder is assembled, the abrasive stratum including a center portion and a periphery, wherein the form and the frame engage and contact the abrasive stratum only at the periphery of the abrasive stratum, wherein the form includes a portion that portrudes out and away from the frame through a central opening in the frame and away from the cap such that it is configured to abut only the periphery of the abrasive stratum and to shape the center portion of the abrasive stratum to protrude out and away from the frame and away from the cap,
wherein said center portion of said abrasive stratum is unsupported by any underlying structure and deformable relative to said periphery of the abrasive stratum, which is supported by said form.

8. The abrading implement of claim 7, wherein at least one of the cap and the form includes a plurality of nubs configured to engage the abrasive stratum and to compress the abrasive stratum against the frame to keep the abrasive stratum from moving during use when the holder is assembled.

9. The abrading implement of claim 7, wherein the abrasive stratum is disk shaped.

* * * * *